(12) United States Patent
Zhang

(10) Patent No.: US 8,877,720 B2
(45) Date of Patent: Nov. 4, 2014

(54) EPIRUBICIN DERIVATIVES

(75) Inventor: Hesheng Zhang, Tianjin (CN)

(73) Assignees: Tianjin Hemay Bio-Tech Co., Ltd., Tianjin (CN); Tianjin Michele Sci-Tech Development Co., Ltd., Tianjin (CN)

( * ) Notice: Subject to any disclaimer, the term of this patent is extended or adjusted under 35 U.S.C. 154(b) by 120 days.

(21) Appl. No.: 13/508,035

(22) PCT Filed: Nov. 3, 2010

(86) PCT No.: PCT/CN2010/078368
§ 371 (c)(1),
(2), (4) Date: Jul. 30, 2012

(87) PCT Pub. No.: WO2011/054289
PCT Pub. Date: May 12, 2011

(65) Prior Publication Data
US 2013/0131001 A1 May 23, 2013

(30) Foreign Application Priority Data
Nov. 3, 2009 (CN) .......................... 2009 1 0071116

(51) Int. Cl.
| A61K 31/70 | (2006.01) |
| C07H 15/24 | (2006.01) |
| C07H 19/044 | (2006.01) |
| A61K 31/06 | (2006.01) |
| C07H 19/04 | (2006.01) |
| C07H 17/02 | (2006.01) |
| C07H 15/252 | (2006.01) |
| C07H 19/048 | (2006.01) |

(52) U.S. Cl.
CPC .............. C07H 19/044 (2013.01); A61K 31/06 (2013.01); C07H 19/04 (2013.01); C07H 17/02 (2013.01); C07H 15/252 (2013.01); C07H 19/048 (2013.01)
USPC ............................................. 514/34; 536/6.4

(58) Field of Classification Search
USPC ........................................................ 536/6.4
See application file for complete search history.

(56) References Cited

FOREIGN PATENT DOCUMENTS

| CN | 101555264 A | 10/2009 |
| GB | 2 140 006 A | 11/1984 |
| JP | 59212484 A | 12/1984 |
| WO | 90/10639 A | 9/1990 |

OTHER PUBLICATIONS

Kristen. M "Epirubicin Hydrochloride (Ellence) Side Effects, Indications, Interactions, Dose Prescribing Information", Google, Dec. 17, 2010.*
PCT application No. PCT/CN2010/078368, International Search Report, mailed Feb. 24, 2011, 3 pages.

* cited by examiner

*Primary Examiner* — Elli Peselev
(74) *Attorney, Agent, or Firm* — Kilpatrick Townsend & Stockton LLP

(57) ABSTRACT

Disclosed are compounds represented by formula (I), pharmaceutically acceptable salts thereof, solvates thereof, and solvates of the pharmaceutically acceptable salts thereof,

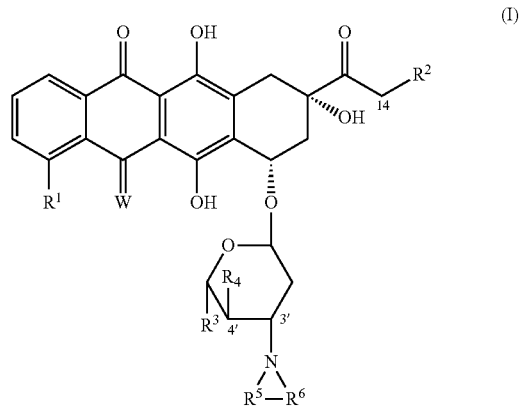

wherein $R^1$, $R^2$, $R^3$, $R^4$, W and

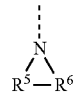

are as defined in the present application.

14 Claims, No Drawings

EPIRUBICIN DERIVATIVES

FIELD

The present application is a U.S. National Phase of PCT/CN2010/078368, filed Nov. 3, 2010, which claims benefit of Chinese Patent Application No. 200910071116.3, filed Nov. 3, 2009, each of which are incorporated by reference for all purposes.

BACKGROUND

Epirubicin (EPI) is an anti-tumor anthracycline antibiotic, which was semisynthesized by the Italian Scientists Arcamone, et al in 1975. The difference between epirubicin and adriamycin only resides in that the hydroxyl at 4-position of glycosamine moiety is changed from cis-form to trans-form. However, such a small change in stereochemistry results in significant reduction in toxicity on heart and marrow.

The main action of epirubicin is that it directly inserts into base pairs of DNA to interfere the transcription process and prevent the formation of mRNA. Epirubicin can inhibit the synthesis of DNA and RNA and therefore has effects on all stages of a cell cycle. Epirubicin is a cell cycle nonspecific agent. Epirubicin can affect both the cell membrane and the transport system. However, the most important site of action is nucleus. Furthermore, epirubicin can also inhibit topoisomerase II.

Epirubicin has equal to or higher anti-tumor activity comparing with adriamycin (ADM), while having lower toxic effects, especially lower toxicity on heart. It has been demonstrated that epirubicin has broad spectrum anti-tumor effects in experiments. Clinically, epirubicin is mainly used to treat leukemia, malignant lymphoma, multiple myeloma, breast cancer, soft tissue sarcoma, gastric cancer, liver cancer, colorectal cancer, ovarian cancer and the like. Comparing with adriamycin, epirubicin has relatively lower toxicity, but still results in myocardial injury and heart failure. It is shown in comparative studies that the ratio of accumulative dose causing the same degree of heart hypofunction of epirubicin to adriamycin is 2:1. Therefore, the heart function should be still carefully monitored during the treatment with epirubicin, such that the risks for heart failure can be reduced (such a heart failure even occurs several weeks later after the treatment stops and may be of no effects on the corresponding drug treatment). As to patients that are currently receiving or has received the concomitant radiotherapy for mediastinum and pericardial regions, the potential risks for heart toxicity of epirubicin may increase and may has marrow inhibition, gastrointestinal reaction such as nausea, vomiting, etc, skin reaction such as dermatitis, pigmentation, etc, and toxic side effects such as phlebitis, cellulitis, etc.

SUMMARY

In one aspect, the present application is directed to a compound represented by formula (I), a pharmaceutically acceptable salt thereof, a solvate thereof, or a solvate of the pharmaceutically acceptable salt thereof,

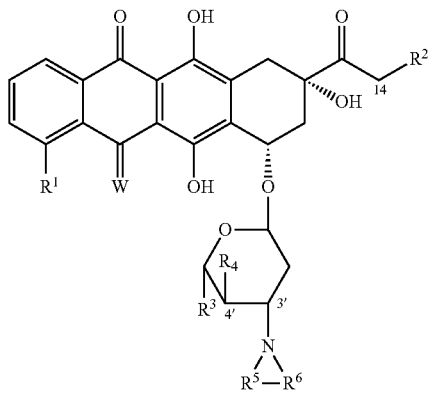

wherein:
$R^1$ represents H, F, OH, optionally substituted hydrocarbyl or optionally substituted hydrocarboxy;
$R^2$ represents H or OH;
W represents O or NH;
$R^3$ represents H, F, OH, optionally substituted hydrocarbyl or optionally substituted hydrocarboxy;
$R^4$ represents F or $OR^7$, wherein $R^7$ represents H or 2-pyranyl;

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings.

In another aspect, the present application is directed to a pharmaceutical composition comprising a pharmaceutically acceptable carrier and a therapeutically effective amount of a compound represented by formula (I), a pharmaceutically acceptable salt thereof, a solvate thereof, or a solvate of the pharmaceutically acceptable salt thereof,

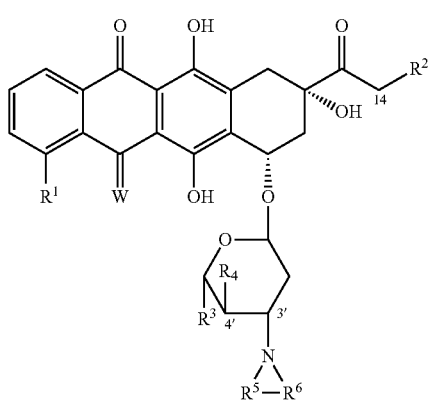

wherein:

R¹ represents H, F, OH, optionally substituted hydrocarbyl or optionally substituted hydrocarboxy;
R² represents H or OH;
W represents O or NH;
R³ represents H, F, OH, optionally substituted hydrocarbyl or optionally substituted hydrocarboxy;
R⁴ represents F or OR⁷, wherein R⁷ represents H or 2-pyranyl;

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings.

In yet another aspect, the present application is directed to a process for preparing a compound represented by formula (I), a pharmaceutically acceptable salt thereof, a solvate thereof, or a solvate of the pharmaceutically acceptable salt thereof,

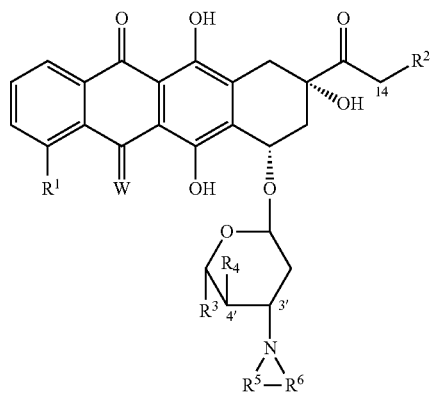

(I)

wherein:

R¹ represents H, F, OH, optionally substituted hydrocarbyl or optionally substituted hydrocarboxy;
R² represents H or OH;
W represents O or NH;
R³ represents H, F, OH, optionally substituted hydrocarbyl or optionally substituted hydrocarboxy;
R⁴ represents F or OR⁷, wherein R⁷ represents H or 2-pyranyl;

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings, the process comprising:

reacting a compound represented by formula (VII) or a salt formed from a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula (VIII) to obtain a compound represented by formula (I) in presence of an acidic agent or/and a basic agent,

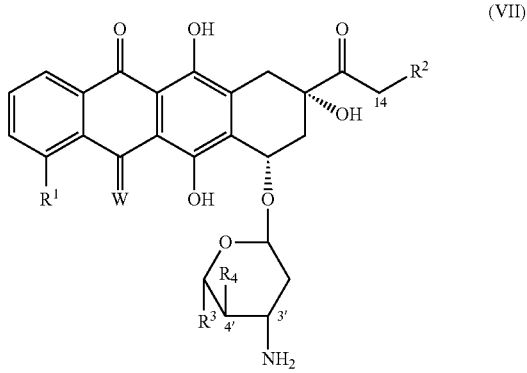

(VII)

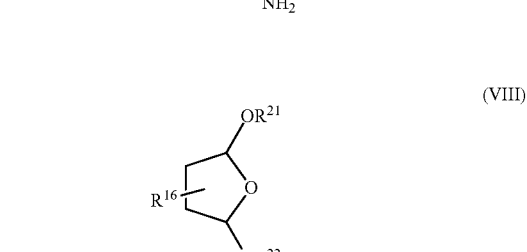

(VIII)

wherein R¹, R², R³, R⁴ and W groups in formula (VII) are identical to R¹, R², R³, R⁴ and W groups in formula (I), R¹⁶ group in formula (VIII) is identical to R¹⁶ group in formula (VI), and R²¹ and R²² separately represent H or optionally substituted hydrocarbyl; or reacting a compound represented by formula (VII) or a salt formed from a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula (IX) to obtain a compound represented by formula (X), and giving a compound represented by formula (I) by subjecting the compound represented by formula (X) to a dehydrating agent,

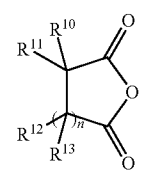

(IX)

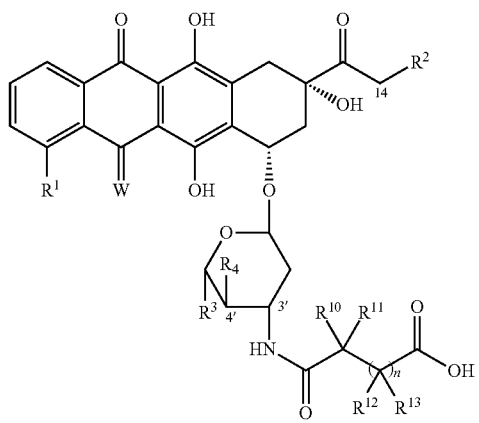

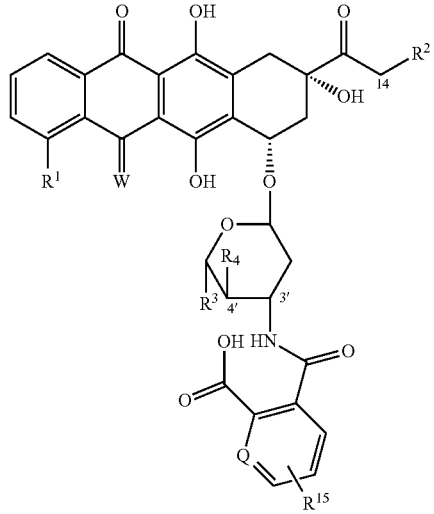

wherein $R^{10}$, $R^{11}$, $R^{21}$, $R^{13}$ groups and n in formula (IX) are identical to $R^{10}$, $R^{11}$, $R^{12}$, $R^{13}$ groups and n in formula (II); $R^{10}$, $R^{11}$, $R^{12}$, $R^{13}$ groups and n in formula (X) are identical to $R^{10}$, $R^{11}$, $R^{12}$, $R^{13}$ groups and n in formula (II), and $R^1$, $R^2$, $R^3$, $R^4$ and W groups in formula (X) are identical to $R^1$, $R^2$, $R^3$, $R^4$ and W groups in formula (VII); or reacting a compound represented by formula (VII) or a salt formed from a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula ⑧ to obtain a compound represented by formula ⑨ or ⑩, and giving a compound represented by formula (I) by subjecting the compound represented by formula ⑨ or ⑩ to a dehydrating agent, wherein $R^{15}$ and Q groups in formula ⑧ are identical to $R^{15}$ and Q groups in formula (V), $R^{15}$ and Q groups in formula ⑨ are identical to $R^{15}$ and Q groups in formula (V), $R^1$, $R^3$, $R^4$, $R^2$ and W groups in formula ⑨ are identical to $R^1$, $R^3$, $R^4$, $R^2$ and W groups in formula (VII), $R^{15}$ and Q groups in formula ⑩ are identical to $R^{15}$ and Q groups in formula (V), and $R^1$, $R^3$, $R^4$, $R^2$ and W groups in formula ⑩ are identical to $R^1$, $R^3$, $R^4$, $R^2$ and W groups in formula (VII).

In another aspect, the present application is directed to a method for treating diseases or conditions caused by abnormal cell proliferation, comprising administering to a subject in need thereof a therapeutically effective amount of a compound of formula (I), a pharmaceutically acceptable salt thereof, a solvate thereof, or a solvate of the pharmaceutically acceptable salt thereof,

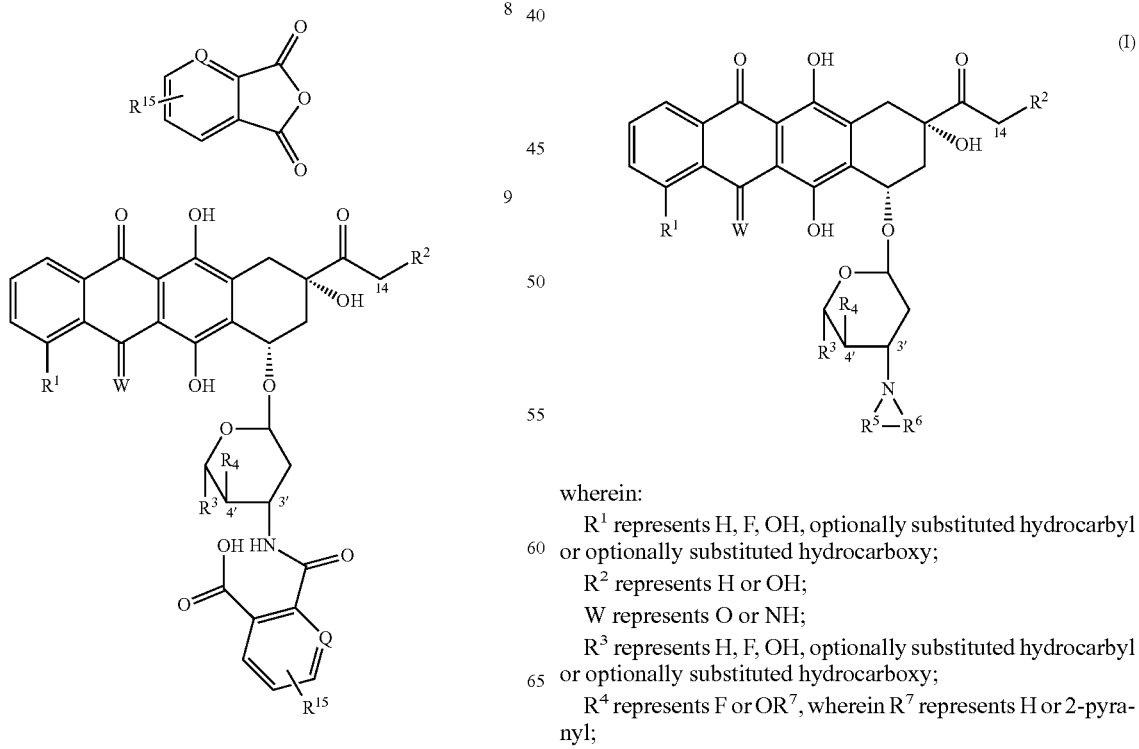

wherein:
$R^1$ represents H, F, OH, optionally substituted hydrocarbyl or optionally substituted hydrocarboxy;
$R^2$ represents H or OH;
W represents O or NH;
$R^3$ represents H, F, OH, optionally substituted hydrocarbyl or optionally substituted hydrocarboxy;
$R^4$ represents F or $OR^7$, wherein $R^7$ represents H or 2-pyranyl;

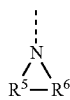

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings.

DETAILED DESCRIPTION

In the following description, certain specific details are included to provide a thorough understanding of various disclosed embodiments. One skilled in the relevant art, however, will recognize that the embodiments may be practiced without one or more these specific details, or with other methods, components, materials, etc.

Unless the context required otherwise, throughout the specification and claims which follows, the term "comprise" and variation thereof, such as "comprises" and "comprising" are to be construed in an open, inclusive sense, which is as "include, but not limited to".

Reference throughout this specification to "one embodiment", or "an embodiment", or "in another embodiment", or "in some embodiments" means that a particular referent feature, structure or characteristic described in connection with the embodiment is included in at least one embodiment. Therefore, the appearance of the phrases "in one embodiment" or "in the embodiment" or "in another embodiment" or "in some embodiments" in various places throughout this specification are not necessarily all referring to the same embodiment. Moreover, the particular features, structures or characteristics may be combined in any suitable manner in one or more embodiments.

It should be noted that, as used in this specification and the appended claims, the singular forms "a", "an" and "the" include plural referents unless the context clearly stated otherwise. Therefore, for example, a reaction comprising "a catalyst" comprises one catalyst, two or more catalysts. It should be also noted that the use of "or" means "and/or" unless stated otherwise.

Definitions

Certain chemical groups named herein are preceded by a shorthand notation indicating the total number of carbon atoms that are to be found in the indicated chemical groups. For example, $C_7$-$C_{12}$ alkyl describes an alkyl as defined below, having a total of 7 to 12 carbon atoms, and $C_4$-$C_{12}$ cyclohydrocarbylalkyl describes a cyclohydrocarbylalkyl, as defined below, having a total of 4 to 12 carbon atoms. The total number of carbon atoms in the shorthand notation does not include carbons that may exist in the substituents of the groups described.

Accordingly, as used in the specification and appended claims, unless specified to the contrary, the following terms have the meanings indicated:

As used herein, the term "hydrocarbyl" refers to an aliphatic hydrocarbon group. The hydrocarbyl moiety may be a "saturated alkyl" group, which means that it does not contain any alkene or alkyne moieties. The hydrocarbyl moiety may also be an "unsaturated alkyl" moiety, which means that it contains at least one alkene or alkyne moiety. An "alkene" moiety refers to a straight or branched hydrocarbon chain group consisting of from two to eight carbon atoms and at least one carbon-carbon double bond, which is attached to the rest of the molecule by a single bond, e.g. ethenyl, prop-1-enyl, but-1-enyl, pent-1-enyl, pent-1,4-dienyl and the like. An "alkyne" moiety refers to a straight or branched hydrocarbon chain group consists of from two to eight carbon atoms and at least one carbon-carbon triple bond, which is attached to the rest of the molecule by a single bond. The hydrocarbyl moiety, whether saturated or unsaturated, may be branched chain or straight chain.

The hydrocarbyl group may have 1 to 20 carbon atoms (whenever it appears herein, a numerical range such as "1 to 20" refers to each integer in the given number range; e.g. "1 to 20 carbon atoms" means that the hydrocarbyl group may consist of 1 carbon atom, 2 carbon atoms, 3 carbon atoms, etc., up to and including 20 carbon atoms, although the present definition also covers the occurrence of term "hydrocarbyl" where no numerical range is designated). The hydrocarbyl group may also be a medium size hydrocarbyl having 1 to 10 carbon atoms. The hydrocarbyl group may also be a lower hydrocarbyl having 1 to 5 carbon atoms. The hydrocarbyl group of compounds of the present application may be designated as "$C_1$-$C_4$ hydrocarbyl" or similar designations. By way of example only, "$C_1$-$C_4$ hydrocarbyl" indicates that there are 1 to 4 carbon atoms in the hydrocarbyl chain, i.e. the hydrocarbyl chain is selected from the group consisting of methyl, ethyl, propyl, isopropyl, n-butyl, iso-butyl, sec-butyl, or t-butyl.

The hydrocarbyl group may be optionally substituted, i.e. substituted or unsubstituted. When substituted, the substituted group(s) is(are) individually and independently selected from cyclohydrocarbyl, aryl, heteroaryl, heteroalicyclic, hydroxy, alkoxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyano, isothiocyanato, nitro, silyl, trihalomethanesulfonyl, —NR'R" or amino including mono- and bi-substituted amino group, and the protected derivatives thereof. Typical hydrocarbyl groups include, but are in no way limited to, methyl, ethyl, propyl, isopropyl, butyl, isobutyl, t-butyl, pentyl, hexyl, ethenyl, propenyl, buenyl, cyclopropyl, cyclobutyl, cyclopentyl, cyclohexyl, and the like. Whenever a substituted is described as being "optionally substituted", that substituent may be substituted with one of the above substituents.

"$C_1$-$C_4$ hydrocarbyl" refers to a hydrocarbyl group as defined above containing 1 to 4 carbon atoms. $C_1$-$C_4$ hydrocarbyl group may be optionally substituted as defined for a hydrocarbyl group.

"$C_1$-$C_6$ hydrocarbyl" refers to a hydrocarbyl group as defined above containing 1 to 6 carbon atoms. $C_1$-$C_6$ hydrocarbyl group may be optionally substituted as defined for a hydrocarbyl group.

"$C_1$-$C_{12}$ hydrocarbyl" refers to a hydrocarbyl group as defined above containing 1 to 12 carbon atoms. $C_1$-$C_{12}$ hydrocarbyl group may be optionally substituted as defined for a hydrocarbyl group.

"$C_2$-$C_6$ hydrocarbyl" refers to a hydrocarbyl group as defined above containing 2 to 6 carbon atoms. $C_2$-$C_6$ hydrocarbyl group may be optionally substituted as defined for a hydrocarbyl group.

"$C_3$-$C_6$ hydrocarbyl" refers to a hydrocarbyl group as defined above containing 3 to 6 carbon atoms. $C_3$-$C_6$ hydrocarbyl group may be optionally substituted as defined for a hydrocarbyl group.

"$C_3$-$C_{12}$ hydrocarbyl" refers to a hydrocarbyl group as defined above containing 3 to 12 carbon atoms. $C_3$-$C_{12}$ hydrocarbyl group may be optionally substituted as defined for a hydrocarbyl group.

"$C_6$-$C_{12}$ hydrocarbyl" refers to a hydrocarbyl group as defined above containing 6 to 12 carbon atoms. $C_6$-$C_{12}$ hydrocarbyl group may be optionally substituted as defined for a hydrocarbyl group.

"$C_7$-$C_{12}$ hydrocarbyl" refers to a hydrocarbyl group as defined above containing 7 to 12 carbon atoms. $C_7$-$C_{12}$ hydrocarbyl group may be optionally substituted as defined for a hydrocarbyl group.

As used herein, "hydrocarboxy" refers to the formula —OR, wherein R is a hydrocarbyl group defined as above, e.g. methoxy, ethoxy, n-propoxy, 1-methyl ethoxy (isopropoxy), n-butoxy, iso-butoxy, sec-butoxy, t-butyoxy, amoxy, t-amoxy, and the like.

As used herein, the term "heterocyclic hydrocarbyl" refers to a stable 3- to 12-membered non-aromatic ring group which consists of carbon atoms and from one to five heteroatoms selected from the group consisting of nitrogen, oxygen and sulphur. Examples of such heterocyclic hydrocarbyl groups include, but are not limited to, dioxolanyl, decahydroisoquinolyl, imidazolinyl, imidazolidinyl, isothiazolidinyl, isooxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl and 1,1-dioxothiomorpholinyl. Unless stated otherwise specifically in the specification, the term "heterocyclic hydrocarbyl" is meant to include heterocyclic hydrocarbyl groups as defined above which are optionally substituted by one or more substituents selected from the group consisting of cyclohydrocarbyl, aryl, heteroaryl, heteroalicyclic, hydroxy, alkoxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyanato, isothiocyanato, nitro, silyl, trihalomethanesulfonyl, —NR'R" (R' and R" are hydrocarbyl groups as defined in the present application) or amino including mono- and di-substituted amino group, and the protected derivatives thereof.

As used herein, the term "heteroaryl" refers to a 5- to 18-membered aromatic ring group which consists of carbon atoms and from 1 to 5 heteroatoms selected from the group consisting of nitrogen, oxygen and sulphur. The nitrogen, carbon or sulphur atom in the heteroaryl group can be optionally oxidized, and the nitrogen atom may be optionally quaternized. The examples include, but are not limited to, azepinyl, acridinyl, benzimidazolyl, benzothiazolyl, benzoindolyl, benzothiadiazolyl, benzonaphthofuranyl, benzoxazolyl, benzodioxolyl, benzodioxinyl, benzopyranyl, benzopyronyl, benzofuranyl, benzofuranonyl, benzothienyl (benzophenylthio), benzotriazolyl, benzo[4,6]imidazo[1,2-a]pyridyl, carbazolyl, cinnolinyl, dibenzofuranyl, furyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, 2,3-phthalazinonyl, pteridinyl, purinyl, pyrrolyl, pyrazolyl, pyridyl, pyrazinyl, pyrimidinyl, pyridazinyl, quinazolinyl, quinoxalinyl. quinolinyl, quinuclidinyl, isoquinolinyl, thiazolyl, thiadiazolyl, triazolyl, tetrazolyl, triazinyl and thiophenyl. Unless stated otherwise specifically in the specification, the term "heteroaryl" is meant to include heterocyclic hydrocarbyl groups as defined above which are optionally substituted by one or more substituents selected from the group consisting of cyclohydrocarbyl, aryl, heteroaryl, heteroalicyclic, hydroxy, alkoxy, aryloxy, mercapto, hydrocarbylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxyl, O-carboxyl, isocyanato, thiocyanato, isothiocyanato, nitro, silyl, trihalomethanesulfonyl, —NR'R" (R' and R" are hydrocarbyl groups as defined in the present application) or amino including mono- and di-substituted amino group, and the protected derivatives thereof.

"Optional" or "optionally" means that the subsequently described event of circumstances may or may not occur, and that the description includes instances where said event or circumstance occurs and instances, in which it does not. For example, "optionally substituted aryl" means that the aryl group may or may not be substituted and the description includes both substituted aryl groups and aryl groups having no substitution.

"Pharmaceutically acceptable carrier" includes without limitation any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and have no side effect on preparing a pharmaceutical composition.

"Pharmaceutically acceptable salts" include both "pharmaceutically acceptable acid addition salts" and "pharmaceutically acceptable base addition salts".

"A pharmaceutically acceptable acid addition salt" refers to those salts which retain the biological effectiveness and properties of the free bases, which are not biologically or otherwise undesirable, and which are formed with inorganic acids such as, but not limited to hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid and the like.

"Pharmaceutically acceptable base addition salt" refers to those salts which retain the biological effectiveness and properties of the free acids, which are not biologically or otherwise undesirable. These salts are prepared from addition of an inorganic or an organic base to the free acid. Salts derived from inorganic bases include, but are not limited to, sodium, potassium, lithium, ammonium, calcium, magnesium, iron, zinc, copper, manganese, aluminum slats, and the like. Preferred inorganic salts are the ammonium, sodium, potassium, calcium, and magnesium salts. Salts derived from organic bases include, but are not limited to, slats of primary, secondary and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminethanol, dicyclohexylamine, lysine, arginine, histidine, caffeine, procaine, hydrabamine, choline, betaine, benethamine, benzathine, ethylenediamine, glucosamine, methylglucosamine, theobromine, triethanolamine, trometamol, purine, piperazine, piperidine, N-ethyl piperidine, polyamine resin and the like. Particularly preferred organic bases are isopropylamine, diethylamine, ethanolamine, trimethylamine, dicyclohexylamine, choline and caffeine.

Often crystallizations produce a solvate of the compound of the present application. As used herein, the term "solvate" refers to an aggregate that comprises one or more molecules of a compound of the present application with one or more molecules of solvent. The solvent may be water, in which cases the solvate may be a hydrate. Alternatively, the solvent may be an organic solvent. Therefore, the compounds of the present application may exist as a hydrate, including monohydrate, dihydrate, hemihydrate, sesquihydrate, trihydrate, tetrahydrate and the like, as well as the corresponding solvated forms. The compound of the present application may be true solvate, while in other cases, the compound of the present application may merely retain adventitious water or be a mixture of water plus some adventitious solvent.

A "pharmaceutical composition" refers to a formulation of a compound of the present application and a medium generally acceptable in the art for the delivery of the biologically active compound to mammals, e.g. humans. Such a medium includes all pharmaceutically acceptable carriers, diluents or excipients therefor.

"Therapeutically effective amount" refers to that amount of a compound of the present application which, when administered to a mammal, preferably a human, is sufficient to effect treatment, as defined below, of diseases or conditions caused by abnormal cell proliferation in a mammal, preferably a human. The amount of a compound of the present application which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e. arresting its development; or (iii) relieving the disease or condition, i.e. causing regression of the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

Specific Embodiments

In one aspect, the present application is directed to a compound represented by formula (I), a pharmaceutically acceptable salt thereof, a solvate thereof, or a solvate of the pharmaceutically acceptable salt thereof,

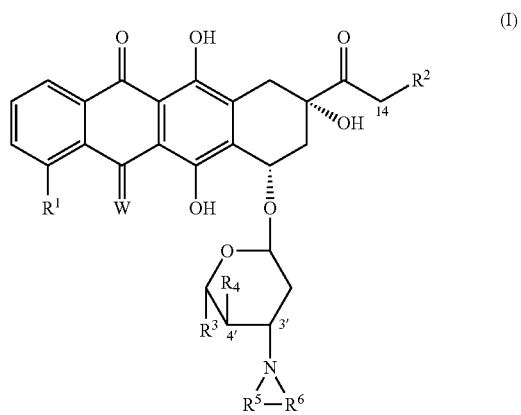

wherein:

$R^1$ represents H, F, OH, optionally substituted hydrocarbyl or optionally substituted hydrocarboxy;

$R^2$ represents H or OH;

W represents O or NH;

$R^3$ represents H, F, OH, optionally substituted hydrocarbyl or optionally substituted hydrocarboxy;

$R^4$ represents F or $OR^7$, wherein $R^7$ represents H or 2-pyranyl;

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings.

In some embodiments, $C_1$-$C_8$ hydrocarbyl is selected from the group consisting of $C_1$-$C_4$ hydrocarbyl and $C_1$-$C_6$ hydrocarbyl.

In some embodiments, $C_1$-$C_8$ hydrocarbyl is selected from the group consisting of $C_1$-$C_8$ alkyl, $C_2$-$C_8$ alkenyl and $C_2$-$C_8$ alkynyl.

In some embodiments, $C_1$-$C_8$ hydrocarbyl is selected from the group consisting of $C_1$-$C_6$ alkyl, $C_2$-$C_6$ alkenyl and $C_2$-$C_6$ alkynyl.

In some embodiments, $C_1$-$C_8$ hydrocarbyl is selected from the group consisting of $C_1$-$C_4$ alkyl, $C_2$-$C_4$ alkenyl and $C_2$-$C_4$ alkynyl.

In some embodiments, $C_1$-$C_8$ hydrocarboxy is selected from the group consisting of $C_1$-$C_4$ hydrocarboxy and $C_1$-$C_6$ hydrocarboxy.

In some embodiments, $C_1$-$C_8$ hydrocarboxy is selected from the group consisting of $C_1$-$C_8$ alkoxy, $C_1$-$C_6$ alkoxy, or $C_1$-$C_4$ alkoxy.

In some embodiments, $R^1$ represents H, $CH_3$, or $OCH_3$.

In some embodiments, $R^3$ represents H, F, $CH_3$, $CH_2CH_3$, OH, $OCH_3$, or $OCH_2CH_3$.

In some embodiments, $R^3$ represents H, $CH_3$, OH, or $OCH_3$.

In some embodiments, $R^3$ represents $CH_3$.

In some embodiments, the optionally substituted saturated heterocyclic hydrocarbyl, optionally substituted unsaturated heterocyclic hydrocarbyl, optionally substituted aromatic heterocyclyl or optionally substituted fused cyclic group further comprises one or two identical or different other heteroatoms.

In some embodiments, the optionally substituted saturated heterocyclic hydrocarbyl, optionally substituted unsaturated heterocyclic hydrocarbyl, optionally substituted aromatic heterocyclyl or optionally substituted fused cyclic group further comprises one or two identical or different heteroatoms selected from the group consisting of nitrogen, oxygen or sulphur atom.

In some embodiments,

is selected from the group consisting of a group represented by formula (II), a group represented by formula (V) and a group represented by formula (VI),

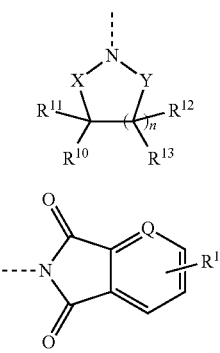

wherein n represents 1 or 2; X represents C=O or $CR^{21}R^{22}$; Y represents C=O or $CR^{21}R^{22}$; Q represents CH or N; $R^{10}$, $R^{11}$, $R^{12}$, $R^{13}$, $R^{15}$, $R^{16}$, $R^{21}$ and $R^{22}$ separately represent H, F, Cl, CN, OH, $COOC_{1-4}$ hydrocarbyl, $OC_{1-4}$ hydrocarbyl, $C_{1-4}$ hydrocarbyl or $NR^{18}R^{19}$; $R^{18}$ and $R^{19}$ separately represent H or $C_{1-6}$ hydrocarbyl, or $NR^{18}R^{19}$ together represents pyrrolidin-1-yl, piperidin-1-yl or morpholin-1-yl.

In some embodiments,

represents a group represented by formula (VI),

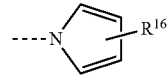

wherein $R^{16}$ represents H, F, Cl, CN, OH, $CH_3$, $CH_2CH_3$, $CH_2CH_2CH_3$, $OCH_3$, $OCH_2CH_3$, $OCH_2CH_2CH_3$, $COOCH_3$, $COOCH_2CH_3$, $COOCH_2CH_2CH_3$, $N(CH_3)_2$, $N(CH_2CH_3)_2$, pyrrolidin-1-yl, piperidin-1-yl or morpholin-1-yl.

In some embodiments,

represents 1-pyrrolyl, succinimidyl, glutarimido, butyrolactam-1-yl, valerolactam-1-yl, 3-methyl-pyrrol-1-yl, 3-methoxyl-pyrrol-1-yl, 3-methyl-succinimidyl, 3-methoxyl-succinimidyl, 3-methyl-glutarimido, 3-methoxyl-glutarimido, 3-methyl-butyrolactam-1-yl, 3-methoxyl-butyrolactam-1-yl, 3-methyl-valerolactam-1-yl, 3-methoxy-valerolactam-1-yl, 4-methyl-valerolactam-1-yl, 4-methoxyl-valerolactam-1-yl, 2-cyanomorpholinyl, 2-pyrrolin-1-yl, or phthalimido.

In some embodiments,

represents 1-pyrrolyl, succinimidyl, glutarimido, butyrolactam-1-yl, or valerolactam-1-yl.

In another aspect, the present application is directed to a pharmaceutical composition comprising a pharmaceutically acceptable carrier and a therapeutically effective amount of a compound represented by formula (I), a pharmaceutically acceptable salt thereof, a solvate thereof, or a solvate of the pharmaceutically acceptable salt thereof,

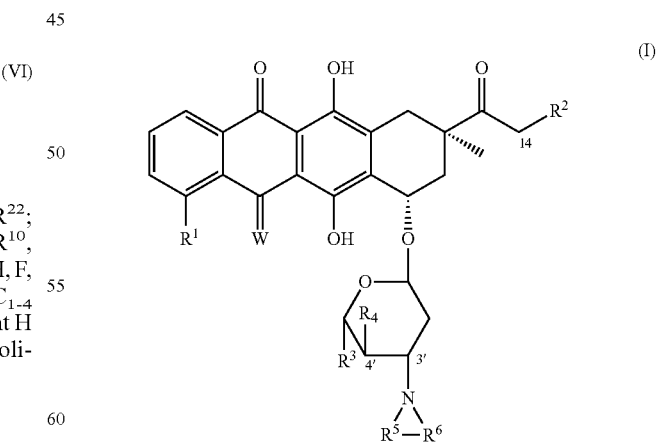

wherein:
$R^1$ represents H, F, OH, optionally substituted hydrocarbyl or optionally substituted hydrocarboxy;
$R^2$ represents H or OH;
W represents O or NH;

$R^3$ represents H, F, OH, optionally substituted hydrocarbyl or optionally substituted hydrocarboxy;

$R^4$ represents F or $OR^7$, wherein $R^7$ represents H or 2-pyranyl;

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings.

In some embodiments, the pharmaceutical composition is formulated into a dosage form suitable for oral administration, buccal administration, intravenous injection, intraperitoneal injection, subcutaneous injection, intramuscular injection, nasal drops, eye drops, inhalation, rectal administration, vaginal administration or epidermal administration.

In some embodiments, the pharmaceutical composition is formulated into a solution, a water for injection, a powder for injection, a lyophilized powder for injection, an oral solution, a syrups, tablets, pills, capsules, granules, gels, softgels, suppositories, aerosols or creams.

In some embodiments, the pharmaceutical composition is formulated into a powder injection, a lyophilized powder injection, a water injection, an emulsion or a suspension.

In some embodiments, the pharmaceutical composition further comprises excipients, lubricants, disintegrants, glidants, solubilizers, fillers, solvents, diluents, suspending agents, osmoregulators, buffers, analgesics, preservatives, antioxidants, sweetening agents, colorants and/or binders.

Exemplary solubilizers that can be used in the present application include, but are not limited to, polyethyleneglycols (which include, but are not limited to, polyethyleneglycol 400, polyethyleneglycol 600 and polyethyleneglycol 2000), Tweens (which include, but are not limited to, Tween 20, Tween 40 and Tween 80), polyoxyethylene castor oil, polyoxyethylene hydrogenated castor oil, polyvinylpyrrolidone, poloxamer, lecithin, soybean lecithin, cephalin, phosphatidic acid, dipalmitoyl phosphatidylcholine, phosphatidylethanolamines, phosphatidylserine, cholesterol, diaminocholesterol, soyasterol glycoside, propylene glycol, D-mannitol, trehalose, benzyl benzoate, ethanol, triaminomethane, sodium carbonate, sodium citrate, sodium salicylate, sodium acetate, triethanolamine, soyasterol and ergosterol.

Exemplary excipients that can be used in the present application include, but are not limited to, lactose, sugar, D-mannitol, D-sorbitol, starch, α-starch, dextrin, crystalline cellulose, lower substituted hydroxypropylcellulose, sodium carboxymethylcellulose, acacia, amylopectin, light anhydrous silicic acid, synthetic aluminum silicate and magnesium aluminum silicate.

Exemplary lubricants that can be used in the present application include, but are not limited to, magnesium stearate, calcium stearate, talc, silica gel and magnesium lauryl sulfate.

Exemplary binders that can be used in the present application include, but are not limited to, α-starch, sucrose, gelatin, acacia, methylcellulose, ethylcellulose, carboxymethyl cellulose, sodium carboxymethyl cellulose, crystalline cellulose, sugar, D-mannitol, trehalose, dextrin, amylopectin, hydroxypropylcellulose, hydroxypropylmethylcellulose and polyvinylpyrrolidone.

Exemplary disintegrants that can be used in the present application include, but are not limited to, sodium carboxymethyl starch, lower substituted hydroxypropyl cellulose, cross-linked polyvinylpyrrolidone, cross-linked sodium carboxymethyl cellulose, cross-linked sodium carboxymethyl starch and processed agar.

Exemplary glidants that can be used in the present application include, but are not limited to, aerosol, Cab-O-Sil (Cabot Corporation), Arosil (Degussa Corporation) and sodium aluminosilicate hydrate.

Exemplary fillers as described herein include, but are not limited to, lactose, sugar, starch, mannitol, erythritol, powdered sugar, dextrin and microcrystalline cellulose.

Exemplary solvents that can be used in the present application include, but are not limited to, water for injection, physiological saline, Ringer solution, ethanol, propylene glycol, polyethylene glycol, sesame oil, corn oil, olive oil and cotton seed oil.

Exemplary suspending agents that can be used in the present application include, but are not limited to, surfactants, such as stearoylyl triethanolamine, sodium lauryl sulfate, lauryl amino propionic acid, lecithin, benzalkonium chloride, phenylethyl chloride, glycerol monostearate; hydrophilic polymers, such as polyvinyl alcohol, polyvinylpyrrolidone, sodium carboxymethylcellulose, methylcellulose, hydroxymethylcellulose, hydroxyethylcellulose, hydroxypropylcellulose, etc; polysolvate and polyoxyethylene-hardened castor oil.

Exemplary osmoregulators that can be used in the present application include, but are not limited to, sodium chloride, glycerol, D-mannitol, D-sorbitol, glucose, and the like.

Exemplary buffers that can be used in the present application include, but are not limited to, phosphate buffers, acetate buffers, carbonate buffers and citrate buffers.

Exemplary analgesics that can be used in the present application include, but are not limited to phenylcarbinol.

Exemplary preservatives that can be used in the present application include, but are not limited to, p-hydroxylbenzophenone, chlorobutanol, phenylcarbinol, phenylethanol, dehydrogenated acetic acid and sorbic acid.

Exemplary antioxidants that can be used in the present application include, but are not limited to, sulfite and ascorbate.

Exemplary colorants that can be used in the present application include, but are not limited to, soluble edible tartrazine dye (food dyes such as Food Red No. 2 or No. 3, Food Yellow No. 4 or No. 5, Food Blue No. 1 or No. 2); insoluble color-sink dyes (such as aluminum salts of soluble edible tartrazine dyes), sunset yellow, lemon yellow or carmine; and natural dyes (such as beta-carotene, chlorophyll, colcothar).

Exemplary sweetening agents that can be used in the present application include, but are not limited to, natural or synthetic sweetening agents, such as saccharin sodium, glycyrrhetinic dipotassium, xylitol, aspartame, orange solid flavor, sodium cyclamate, sorbitol, sucrose, glucose and stevioside.

In another aspect, the present application is directed to a process for preparing a compound represented by formula (I), a pharmaceutically acceptable salt thereof, a solvate thereof, or a solvate of the pharmaceutically acceptable salt thereof, (I)

[Structure of formula (I): tetracyclic anthracycline with substituents $R^1$, W, OH, OH, O, $R^2$, position 14, and sugar moiety with $R^3$, $R^4$, 3', 4', N–$R^5$–$R^6$]

wherein:
$R^1$ represents H, F, OH, optionally substituted hydrocarbyl or optionally substituted hydrocarboxy;
$R^2$ represents H or OH;
W represents O or NH;
$R^3$ represents H, F, OH, optionally substituted hydrocarbyl or optionally substituted hydrocarboxy;
$R^4$ represents F or $OR^7$, wherein $R^7$ represents H or 2-pyranyl;

[Structure: aziridine-like N with $R^5$–$R^6$]

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings, the process comprising:
reacting a compound represented by formula (VII) or a salt formed from a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula (VIII) to obtain the compound represented by formula (I) in presence of an acidic agent or/and a basic agent, (VII)

[Structure of formula (VII): similar tetracyclic structure with $R^1$, W, OH, OH, O, $R^2$, position 14, sugar with $R^3$, $R^4$, 3', 4', NH$_2$]

(VIII)

[Structure of formula (VIII): tetrahydrofuran ring with $OR^{21}$, $R^{16}$, $OR^{22}$ substituents]

wherein $R^1$, $R^2$, $R^3$, $R^4$ and W groups in formula (VII) are identical to $R^1$, $R^2$, $R^3$, $R^4$ and W groups in formula (I); $R^{16}$ group in formula (VIII) is identical to $R^{16}$ group in formula (VI), and $R^{21}$ and $R^{22}$ separately represent H or optionally substituted hydrocarbyl.

In some embodiments, the salt of a compound represented by formula (VII) is selected from the group consisting of hydrochloride, sulfate, phosphate, formate, acetate, mesylate, esylate, benzene sulfonate and p-tosylate.

In some embodiments, the acidic agent is selected from the group consisting of hydrochloric acid, sulfuric acid, phosphoric acid, formic acid, acetic acid, propionic acid, butyric acid, valeric acid, caproic acid, methanesulfonic acid, ethanesulfonic acid, benzenesulfonic acid, p-toluenesulfonic acid, citric acid, tartaric acid, lactic acid, malic acid and a mixture thereof.

In some embodiments, the amount of an acidic agent is 0.05-500 folds (by mole) of the amount of a compound represented by formula (VII). In some embodiments, the amount of an acidic agent is 0.2-50 folds (by mole) of the amount of a compound represented by formula (VII). In some embodiments, the amount of an acidic agent is 0.7-5 folds (by mole) of the amount of a compound represented by formula (VII).

In some embodiments, the basic agent is selected from the group consisting of potassium carbonate, cesium carbonate, sodium carbonate, sodium bicarbonate, potassium bicarbonate, sodium hydroxide, potassium hydroxide, sodium acetate, potassium acetate, sodium phosphate, potassium phosphate, disodium hydrogen phosphate, dipotassium hydrogen phosphate, sodium lactate, potassium lactate, sodium citrate, potassium citrate, sodium tartrate, potassium tartrate, sodium malate, potassium malate, sodium propionate, potassium propionate, sodium butyrate, potassium butyrate, sodium succinate, potassium succinate, sodium valerate, potassium valerate, sodium glutarate, potassium glutarate and a mixture thereof.

In some embodiments, the amount of a basic agent is 0.05-500 folds (by mole) of the amount of a compound represented by formula (VII). In some embodiments, the amount of a basic agent is 0.2-50 folds (by mole) of amount of a compound represented by formula (VII). In some embodiments, the amount of a basic agent is 0.7-5 folds (by mole) of the amount of a compound represented by formula (VII).

In some embodiments, the reaction temperature is in the range between –10° C. and 150° C. In some embodiments, the reaction temperature is in the range between 0° C. and 100° C. In some embodiments, the reaction temperature is in the range between 10° C. and 80° C.

In some embodiments, the reaction is carried out in a solvent.

Exemplary solvents that can be used in the present application include, but are not limited to, dichloromethane, trichloromethane, N,N-dimethylformamide, dimethylsulfoxide, ethylene glycol dimethyl ether, ethanol, methanol, isopropanol, tetrahydrofuran, ethyl acetate, methyl acetate, methyl propionate, ethyl propionate, ethylene glycol diethyl ether, N,N-diethylformamide, 1,2-dichloroethane, acetonitrile, water and a compound represented by formula (VIII).

In some embodiments, an organic base is added in the reaction as an acid binding agent or a catalyst.

Exemplary organic bases that can be used in the present application include, but are not limited to, triethylamine, trimethylamine, diisopropylethylamine, 4-dimethylaminopyridine, 4-(1-pyrrolidinyl)pyridine, pyridine and N-methylmorpholine.

In some embodiments, the amount of a base, when used as an acid binding agent, is 0.5-10 folds by mole of a compound represented by formula (VII). In some embodiments, the amount of a base, when used as an acid agent, is 1-5 folds by mole of a compound represented by formula (VII).

In some embodiments, the amount of a base, when used as a catalyst, is 0.01-2 folds by mole of a compound represented by formula (VII). In some embodiments, the amount of a base, when used as a catalyst, is 0.05-0.2 folds by mole of a compound represented by formula (VII).

In some embodiments, the molar ratio of a compound represented by formula (VII) or a salt thereof to a compound represented by formula (VIII) is 1:0.1 to 1:10000. In some embodiments, the molar ratio of a compound represented by formula (VII) or a salt thereof to a compound represented by formula (VIII) is 1:0.5 to 1:1000. In some embodiments, the molar ratio of a compound represented by formula (VII) or a salt thereof to a compound represented by formula (VIII) is 1:1 to 1:500.

In yet another aspect, the present application is directed to a process for preparing a compound represented by formula (I), a pharmaceutically acceptable salt thereof, a solvate thereof, or a solvate of the pharmaceutically acceptable salt thereof,

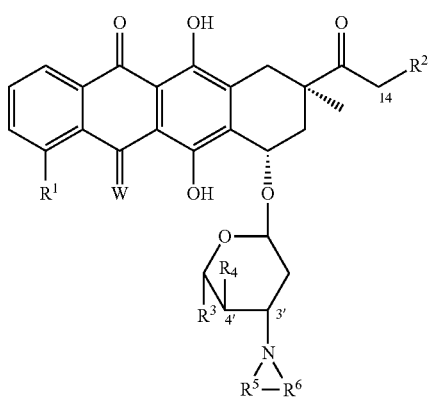

wherein:

$R^1$ represents H, F, OH, optionally substituted hydrocarbyl or optionally substituted hydrocarboxy;

$R^2$ represents H or OH;

W represents O or NH;

$R^3$ represents H, F, OH, optionally substituted hydrocarbyl or optionally substituted hydrocarboxy;

$R^4$ represents F or $OR^7$, wherein $R^7$ represents H or 2-pyranyl;

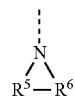

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings, the process comprising:
reacting a compound represented by formula (VII) or a salt formed from a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula (IX) to obtain a compound represented by formula (X), and giving the compound represented by formula (I) by subjecting the compound represented by formula (X) to a dehydrating agent,

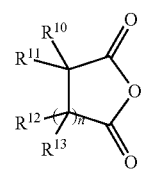

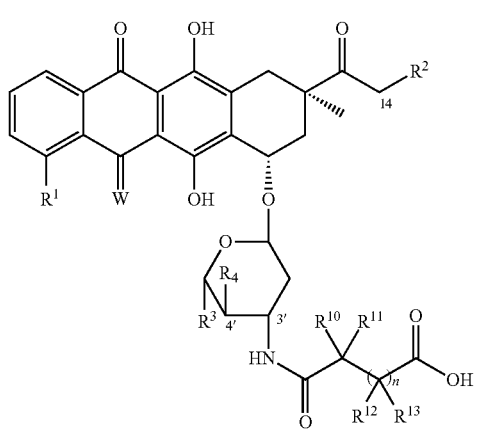

wherein $R^{10}$, $R^{11}$, $R^{12}$, $R^{13}$ groups and n in formula (IX) are identical to $R^{10}$, $R^{11}$, $R^{12}$, $R^{13}$ groups and n in formula (II); $R^{10}$, $R^{11}$, $R^{12}$, $R^{13}$ groups and n in formula (X) are identical to $R^{10}$, $R^{11}$, $R^{12}$, $R^{13}$ groups and n in formula (II); and $R^1$, $R^2$, $R^3$, $R^4$ and W groups in formula (X) are identical to $R^1$, $R^2$, $R^3$, $R^4$ and W groups in formula (VII).

In some embodiments, the reaction is carried out in dichloromethane, trichloromethane, tetrachloromethane, ethyl acetate, methyl acetate, methyl propionate, ethyl propionate, 1,2-dichloroethane, acetone, tetrahydrofuran, ethylene glycol dimethyl ether, ethylene glycol diethyl ether, N,N-dimethylformamide, N,N-diethylformamide, dimethylsulfoxide, acetonitrile, water or a mixture thereof.

In some embodiments, a catalyst is added in the reaction.
Exemplary catalysts that can be used in the present application include, but are not limited to, pyridine, 4-dimethylaminopyridine, 4-diethylaminopyridine and 4-(pyrrolidin-1-yl)-pyridine.

In some embodiments, the amount of a catalyst is 0.01-10 folds by mole of a compound represented by formula (VII). In some embodiments, the amount of a catalyst is 0.02-5 folds by mole of a compound represented by formula (VII). In some embodiments, the amount of a catalyst is 0.05-1 fold by mole of a compound represented by formula (VII).

In some embodiments, an acid binding agent is added in the reaction.

Exemplary acid binding agents that can be used in the present application include, but are not limited to, triethylamine, trimethylamine, pyridine, diisopropylethylamine, N-methylmorpholine, N-methylpiperidine, N-ethylpiperidine, 4-dimethylaminopyridine, 4-diethylaminepyridine, 4-(pyrrolidin-1-yl)-pyridine, potassium carbonate, sodium carbonate, sodium bicarbonate, potassium bicarbonate, cesium carbonate, sodium hydroxide and potassium hydroxide.

In some embodiments, the amount of an acid binding agent is 0.4-20 folds by mole of a compound represented by formula (VII). In some embodiments, the amount of an acid binding agent is 0.8-10 folds by mole of a compound represented by formula (VII). In some embodiments, the amount of an acid binding agent is 1-5 folds by mole of a compound represented by formula (VII).

In some embodiments, the reaction temperature is in the range between −20° C. and 100° C. In some embodiments, the more suitable reaction temperature is in the range between −10° C. and 80° C. In some embodiments, the optimal reaction temperature is in the range between −5° C. and 80° C.

In some embodiments, the molar ratio of a compound represented by formula (IX) to a compound represented by formula (VII) or a salt thereof is 1:0.1 to 1:10. In some embodiments, the molar ratio of a compound represented by formula (IX) to a compound represented by formula (VII) or a salt thereof is 1:0.5 to 1:5. In some embodiments, the molar ratio of a compound represented by formula (IX) to a compound represented by formula (VII) or a salt thereof is 1:0.8 to 1:3.

Exemplary dehydrating agents that can be used in the present application include, but are not limited to, DCC (dicyclohexyl-carbodiimide), EDC HCl (1-ethyl-3-(3-dimethylaminopropyl)carbodiimide hydrochloride), CDI (N,N'-carbonyldiimidazole) and DIC(N,N'-diisopropylcarbodiimide).

In some embodiments, the amount of a dehydrating agent is 0.1-10 folds by mole of a compound represented by formula (X). In some embodiments, the amount of a dehydrating agent is 0.5-5 folds by mole of a compound represented by formula (X). In some embodiments, the amount of a dehydrating agent is 1-3 folds by mole of a compound represented by formula (X).

In some embodiments, the reaction temperature is in the range between −10° C. and 120° C. In some embodiments, the reaction temperature is in the range between 0° C. and 100° C. In some embodiments, the reaction temperature is in the range between 20° C. and 100° C.

In some embodiments, the reaction is carried out in dichloromethane, trichloromethane, ethyl acetate, methyl acetate, ethyl propionate, methyl propionate, acetone, tetrahydrofuran, ethylene glycol dimethyl ether, ethylene glycol diethyl ether, N,N-dimethylformamide, N,N-diethylformamide, dimethylsulfoxide, acetonitrile, or a mixture thereof.

In still another aspect, the present application is directed to a process for preparing a compound represented by formula (I), a pharmaceutically acceptable salt thereof, a solvate thereof, or a solvate of the pharmaceutically acceptable salt thereof,

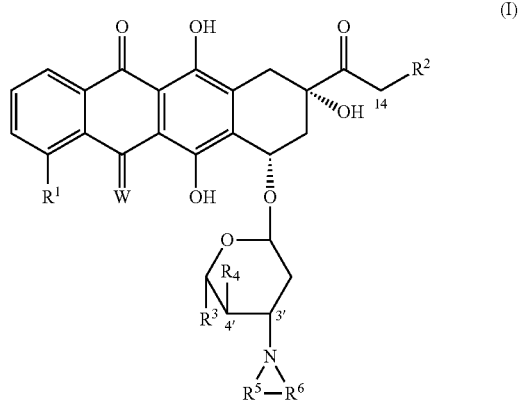

wherein:

$R^1$ represents H, F, OH, optionally substituted hydrocarbyl or optionally substituted hydrocarboxy;

$R^2$ represents H or OH;

W represents O or NH;

$R^3$ represents H, F, OH, optionally substituted hydrocarbyl or optionally substituted hydrocarboxy;

$R^4$ represents F or $OR^7$, wherein $R^7$ represents H or 2-pyranyl;

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings, the process comprising:

reacting a compound represented by formula (VII) or a salt formed from a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula ⑧ to obtain a compound represented by formula ⑨ or ⑩, and giving a compound represented by formula (I) by subjecting the compound represented by formula ⑨ or ⑩ to a dehydrating agent,

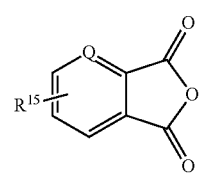

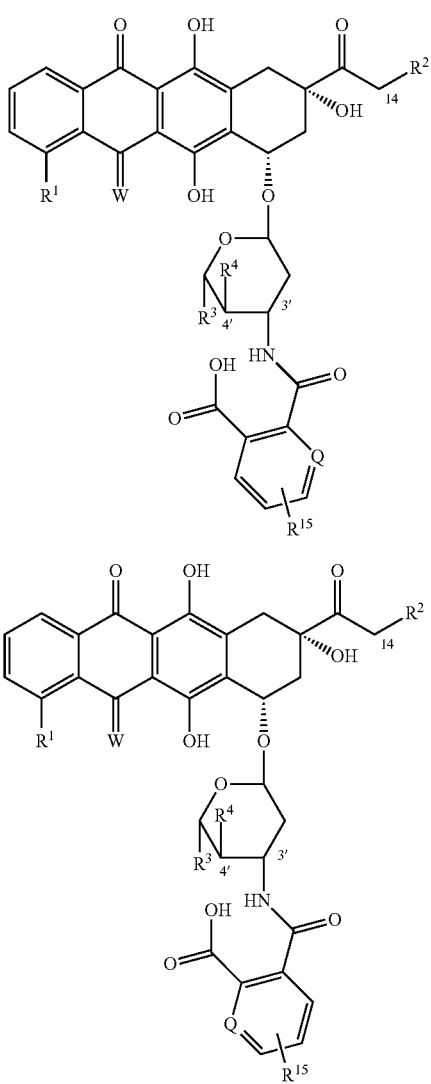

wherein $R^{15}$ and Q groups in formula ⑧ are identical to $R^{15}$ and Q groups in formula (V), $R^{15}$ and Q groups in formula ⑨ are identical to $R^{15}$ and Q groups in formula (V), $R^1$, $R^3$, $R^4$, $R^2$ and W groups in formula ⑨ are identical to $R^1$, $R^3$, $R^4$, $R^2$ and W groups in formula (VII), $R^{15}$ and Q groups in formula ⑩ are identical to $R^{15}$ and Q groups in formula (V), and $R^1$, $R^3$, $R^4$, $R^2$ and W groups in formula ⑦ are identical to $R^1$, $R^3$, $R^4$, $R^2$ and W groups in formula (VII).

In some embodiments, the reaction is carried out in dichloromethane, trichloromethane, tetrachloromethane, ethyl acetate, methyl acetate, methyl propionate, ethyl propionate, 1,2-dichloroethane, acetone, tetrahydrofuran, ethylene glycol dimethyl ether, ethylene glycol diethyl ether, N,N-dimethylformamide, N,N-diethylformamide, dimethylsulfoxide, acetonitrile, water or a mixture thereof.

In some embodiments, a catalyst is added in the reaction.

Exemplary catalysts that can be used in the present application include, but are not limited to, pyridine, 4-dimethylamidopyridine, 4-diethylamidopyridine and 4-(pyrrolidin-1-yl)-pyridine.

In some embodiments, the amount of a catalyst is 0.01-10 folds by mole of a compound represented by formula (VII). In some embodiments, the amount of a catalyst is 0.02-5 folds by mole of a compound represented by formula (VII). In some embodiments, the amount of a catalyst is 0.05-1 fold by mole of a compound represented by formula (VII).

In some embodiments, an acid binding agent is added in the reaction.

Exemplary acid binding agents that can be used in the present application include, but are not limited to, triethylamine, trimethylamine, pyridine, diisopropylethylamine, N-methylmorpholine, N-methylpiperidine, N-ethylpiperidine, 4-dimethylaminopyridine, 4-diethylaminepyridine, 4-(pyrrolidin-1-yl)-pyridine, potassium carbonate, sodium carbonate, sodium bicarbonate, potassium bicarbonate, cesium carbonate, sodium hydroxide and potassium hydroxide.

In some embodiments, the amount of an acid binding agent is 0.4-20 folds by mole of a compound represented by formula (VII). In some embodiments, the amount of an acid binding agent is 0.8-10 folds by mole of a compound represented by formula (VII). In some embodiments, the amount of an acid binding agent is 1-5 folds by mole of a compound represented by formula (VII).

In some embodiments, the reaction temperature is in the range between −20° C. and 100° C. In some embodiments, the reaction temperature is in the range between −10° C. and 80° C. In some embodiments, the reaction temperature is in the range between 0° C. and 80° C.

In some embodiments, the molar ratio of a compound represented by formula (VII) or a salt thereof to a compound represented by formula ⑧ is 1:0.2 to 1:10. In some embodiments, the molar ratio of a compound represented by formula (VII) or a salt thereof to a compound represented by formula ⑧ is 1:0.5 to 1:5. In some embodiments, the molar ratio of a compound represented by formula (VII) or a salt thereof to a compound represented by formula ⑧ is 1:0.8 to 1:3.

Exemplary dehydrating agents that can be used in the present application include, but are not limited to, DCC (dicyclohexylcarbodiimide), EDC HCl (1-ethyl-3-(3-dimethylaminopropyl)carbodiimide hydrochloride), CDI (N,N'-carbonyldiimidazole) and DIC(N,N'-diisopropylcarbodiimide).

In some embodiments, the amount of a dehydrating agent is 0.1-10 folds by mole of a compound represented by formula ⑨ or ⑩. In some embodiments, the amount of a dehydrating agent is 0.5-5 folds by mole of a compound represented by formula ⑨ or ⑩. In some embodiments, the amount of a dehydrating agent is 1-3 folds by mole of a compound represented by formula ⑨ or ⑩.

In some embodiments, the reaction temperature is in the range between −10° C. and 120° C. In some embodiments, the reaction temperature is in the range between 0° C. and 100° C. In some embodiments, the reaction temperature is in the range between 20° C. and 100° C.

In some embodiments, the reaction is carried out in dichloromethane, trichloromethane, ethyl acetate, methyl acetate, ethyl propionate, methyl propionate, acetone, tetrahydrofuran, ethylene glycol dimethyl ether, ethylene glycol diethyl ether, N,N-dimethylformamide, N,N-diethylformamide, dimethylsulfoxide, acetonitrile, or a mixture thereof.

In some embodiments, a catalyst is added in the reaction.

Exemplary catalysts that can be used in the present application include, but are not limited to, pyridine, 4-dimethylaminopyridine, 4-diethylaminopyridine and 4-(pyrrolidin-1-yl)-pyridine.

In some embodiments, the amount of a catalyst is 0.01-1 fold by mole of a compound represented by formula ⑨ or ⑩. In some embodiments, the amount of a catalyst is 0.02-0.8 times fold by mole of a compound represented by formula ⑨ or ⑩. In some embodiments, the amount of a catalyst is 0.03-0.5 fold by mole of a compound represented by formula ⑨ or ⑩.

In yet another aspect, the present application is directed to a method for treating diseases or conditions caused by abnormal cell proliferation, comprising administering to a subject in need thereof a therapeutically effective amount of a compound of formula (I), a pharmaceutically acceptable salt thereof, a solvate thereof, or a solvate of the pharmaceutically acceptable salt thereof,

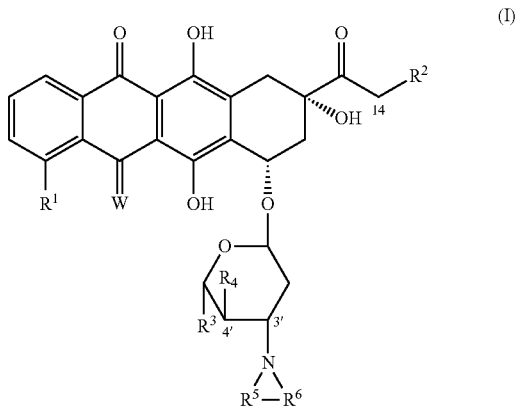

(I)

wherein:

$R^1$ represents H, F, OH, optionally substituted hydrocarbyl or optionally substituted hydrocarboxy;

$R^2$ represents H or OH;

W represents O or NH;

$R^3$ represents H, F, OH, optionally substituted hydrocarbyl or optionally substituted hydrocarboxy;

$R^4$ represents F or $OR^7$, wherein $R^7$ represents H or 2-pyranyl;

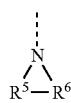

represents 5-, 6- or 7-membered optionally substituted saturated heterocyclic hydrocarbyl comprising one nitrogen atom, optionally substituted unsaturated heterocyclic hydrocarbyl comprising one nitrogen atom or optionally substituted aromatic heterocyclic hydrocarbyl comprising one nitrogen atom, or fused cyclic group consisting of two 5-, 6- or 7-membered rings.

In some embodiments, the diseases or conditions caused by the abnormal cell proliferation are cancer.

In some embodiments, the cancer is selected from the group consisting of prostate cancer, breast cancer, ovarian cancer, liver cancer, stomach cancer, small cell lung cancer, non-small cell lung cancer, intestinal cancer, colon cancer, Hodgkin's disease, non-Hodgkin's lymphoma, rectal cancer, brain cancer, urethral carcinoma, kidney cancer, bladder cancer, uterine cancer, pancreatic cancer, head and neck cancer, melanoma, various leukemia, lymphoma and multiple myeloma.

In some embodiments, a compound of formula (I), a pharmaceutically acceptable salt thereof, a solvate thereof, or a solvate of the pharmaceutically acceptable salt thereof can be used in combination with one or more other compounds for treating diseases or conditions caused by abnormal cell proliferation.

Exemplary others compounds for treating diseases or conditions caused by abnormal cell proliferation that can be used in the present application include, but are not limited to, other sorts of anticancer drugs, immunopotentiators, anticancer synergists, hormones, and traditional Chinese medicine preparations.

In some embodiments, the combination can be carried out simultaneously or sequentially.

Exemplary other compounds for treating diseases or conditions caused by abnormal cell proliferation that can be used in combination with a compound represented by formula (I), a pharmaceutically acceptable salt thereof, a solvate thereof, or a solvate of the pharmaceutically acceptable salt thereof in the present application include, but are not limited to, paclitaxel, cyclophosphamide, 5-fluorouracil, thalidomaide, cisplatin, HKI272, tarceva, Irresa, Actimid, BIBW2992, revlimid (Lenalidomide), triazine derivatives such as hexamethylmelamine; enzyme such as asparaginase; antimicrobial agents such as bleomycin, dactinomycin, daunorubicin, adriamycin, idarubicin, mitomycin, epirubicin or plicamycin; alkylating agents such as busulfan, carboplatin, carmustine, chlorambucil, cisplatin, cyclophosphamide, dacarbazine, ifosfamide, lomustine, chlormethine, phenylalanine chlormethine, procarbazine or thiophosphoramide; antimetabolites such as cladribine, cytarabine, floxuridine, fludarabine, fluorouracil, hydroxyurea, mercaptopurine, methotrexate, gemcitabine, pentostatin or thioguanine; antimitotic agents, such as etoposide, paclitaxel, teniposide, vinblastine, vinorelbine or vincristine; hormone drugs such as aromatase inhibitors such as aminoglutethimide; corticosteroids such as dexamethasone, prednisone or luteinizing hormone released hormone (LH-RH); anti-estrogen agents such as tamoxifen, formestane or letrozole; anti-androgen agents such as flutan; biological response modifiers such as aldesleukin in lymphokine or other interleukins; interferons such as alpha-interferon; growth factors such as erythropoietin, filgrastim or sagramostim; differentiation agents such as vitamin D derivates such as seocalcitol; all-trans retinoic acids; immunomodulators such as levamisole; monoclonal antibodies; tumor necrosis factor α; or angiogenesis inhibitors.

In some embodiments, other compounds for treating diseases or conditions caused by abnormal cell proliferation that can be used in combination with a compound represented by formula (I), a pharmaceutically acceptable salt thereof, a solvate thereof, or a solvate of the pharmaceutically acceptable salt thereof in the present application can be selected from the group consisting of paclitaxel, fluorouracil, etoposide, cyclophosphamide, cisplatin, carboplatin, vincristine, gemcitabine, vinorelbine, chlorambucil, adriamycin, phenylalanine chlormethine, seocalcitol and a mixture thereof.

EXAMPLES

Although anyone skilled in the art is capable of preparing the compounds of the present application according to the general techniques disclosed herein above, more specific details on synthetic techniques for compound of the present application are provided elsewhere in this specification for convenience. Again, all agents and reaction conditions employed in synthesis are known to those skilled in the art and are available from ordinary commercial sources.

The preparation of compounds in the present application is illustrated by, but not limited to, the following examples.

Example 1

3'-pyrrolyl epirubicin

To a 1 L three-neck flask were added 3.076 g of epirubicin hydrochloride, 300 ml of distilled water and 300 ml of 1,2-dichloroethane, 30 ml of 2,5-dimethoxyl tetrahydrofuran and 6 ml of glacial acetic acid. The reaction was heated and refluxed for 45 min under argon atmosphere. The resulting mixture was cooled to the room temperature and poured into 200 ml of ice water. The mixture was stood to separate. The organic phase was washed once with 200 ml of saturated saline, dried over magnesium sulfate, filtered and rotary-evaporated to dryness. To the aqueous phase was added 100 ml of 5% sodium bicarbonate aqueous solution under stirring in an ice bath. The resultant mixture was extracted with chloroform (50 ml×3). The chloroform layers were combined. The combined chloroform layers were washed once with 100 ml of saturated saline, filtered and rotary-evaporated to remove the solvent. The resultant crude product was combined with the crude product obtained above. The combined crude products were purified with column chromatography and eluted with chloroform:methanol=35:1 to give 2.91 g of the object product. MS: 592 (M-1)

Example 2

3'-pyrrolyl epirubicin

To a 1 L three-neck flask were added 3.076 g of epirubicin hydrochloride, 500 ml of distilled water, 30 ml of 2,5-dimethoxyl tetrahydrofuran, 6 ml of glacial acetic acid and 435 mg of sodium acetate. The reaction was carried out for 4 hr at 50° C. under argon atmosphere. The resulting mixture was cooled to the room temperature and vacuum filtered to obtain a filter cake. The filter cake was crystallized to give the object compound. MS: 592 (M-1)

Example 3

3'-pyrrolyl-4'-(pyran-2-yl)epirubicin

3'-pyrrolyl-4'-(pyran-2-yl)epirubicin was obtained from 4'-(pyran-2-yl)epirubicin as a starting material with the process described in Example 1 or 2. MS: 677

Example 4

3'-succinimidyl epirubicin

To a 50 ml of single round-bottom flask was added 100 mg of epirubicin hydrochloride. Epirubicin was dissolved with 3 ml of DMF (N,N-dimethylformamide). Then 63 µl of DIEA (diisopropyl ethyl amine) and 2 mg of DMAP (4-dimethylaminopyridine) were added. The resulting mixture was stirred for 10 min. 21 mg of succinic anhydride were added to the mixture. The resultant mixture was stirred for 1 hr at the room temperature under argon atmosphere. The reaction solution was rotary-evaporated to dryness. 20 ml of distilled water and 10 ml of chloroform were added to the resulting residual. The resultant mixture was vacuum filtered to give a filter cake. The resultant filter cake was dried in vacuo. To a 50 ml of single flask was added 18 mg of the dried filter cake. 5 ml of dichloromethane (dried over molecular sieve) and 12 µl triethylamine (dried over molecular sieve) were added to the flask. 69 mg of cyanuric chloride were then added to the flask. The resulting mixture was stirred overnight at the room temperature. To the reaction solution were added 20 ml of dichloromethane. The resultant mixture was washed once with 20 ml of water. The resultant organic phase was washed with 20 ml of saturated saline. The solvent was rotary evaporated to give a crude product. The crude product was purified with thin layer chromatography and eluted with chloroform:methanol=22:1 to give the object compound. MS: 624 (M-1)

The second process for preparing the object compound: to a 50 ml of single round-bottom flask was added 100 mg of epirubicin hydrochloride. Epirubicin hydrochloride was dissolved with 3 ml of DMF. 63 µl of DIEA (diisopropyl ethyl amine) and 2 mg of DMAP (4-dimethylaminopyridine) were added to the flask. The resulting mixture was stirred for 10 min. 21 mg of succinic anhydride was added to the mixture. The resultant mixture was stirred for 1 hr at the room temperature under argon atmosphere. The reaction solution was rotary evaporated to dryness. 20 ml of distilled water and 10 ml of chloroform were added to the residual. The mixture was vacuum filtered to give a filter cake. The resultant filter cake was dried in vacuo. 18 mg of the dried filter cake was added to a 50 ml of single flask. 5 ml of dichloromethane (dried over molecular sieve) and 28 mg of CDI (carbonyldiimidazole) were added to the flask. The resulting mixture was heated under reflux for 1 hr. To the reaction solution was added 20 ml of dichloromethane. The resultant mixture was washed once with 20 ml of water. The resultant organic phase was washed with 20 ml of saturated saline. The solvent was rotary evaporated to give a crude product. The crude product was purified with thin layer chromatography and eluted with chloroform:methanol=22:1 to give the object compound. MS: 624 (M-1)

The following compounds were prepared according to the process described in Example 4.

Example 5

3'-glutarimido epirubicin MS: 638 (M-1)

Example 6

3'-maleimidyl epirubicin MS: 623

Example 7

3'-(pyridino-(2,3)succinimidyl)epirubicin MS: 674

Example 8

3'-(benzo-(2,3)succinimidyl)epirubicin MS: 673

Example 9

3'-butyrolactamyl epirubicin 10 mg of epirubicin hydrochloride was dissolved in 5 ml of anhydrous DMF. The mixture was cooled to 0° C.-5° C. in an ice bath. 7 mg of diisopropyl ethyl amine was added to the mixture. The resulting mixture was stirred for 10 min. 2.4 mg of 4-chlorobutyryl chloride was added to the resulting mixture. The reaction was performed for 30 min. 100 ml of water was added to the resultant mixture in an ice bath. The resulting mixture was extracted with chloroform three times (5 ml×3). The chloroform layers were combined. The combined layers were washed once with saline, dried over anhydrous magnesium sulfate, filtered and rotary-evaporated to remove the solvent. The resultant product was purified with thin layer chromatography and eluted with chloroform:methanol=95: 5.8 mg of the product were dissolved in 3 ml of anhydrous DMF. The resulting mixture was protected with argon and cooled in an ice bath to a temperature of −5° C. to 0° C. 0.3 mg of sodium hydride was added to the mixture. The resulting mixture was stirred for 24 hr. After the reaction completed, 50 ml of water were added. The resultant mixture was extracted three times with chloroform (5 ml×3). The chloroform layers were combined. The combined layers were washed once with saturated saline, dried over anhydrous magnesium sulfate, filtered and rotary-evaporated to remove the solvent. The product was purified with thin layer chromatography and eluted with chloroform:methanol=30:1 to give 6 mg of the object product. MS: 611

Example 10

Cytotoxicity Assay (MTS Assay)

1. Cell Strains and Reagents
   HePG-2: human liver cancer cell strains
   A549: human lung cancer cell strains
   LOVO: human colon cancer cell strains
   A431: epidermoid cell strains
   THP-1: human leukemia cell strains
   U937: human lymphoma cell strains
   NCI-H460: human lung cancer cell strains
   NCI-H446: human lung cancer cell strains
   DU-145: human prostate cancer cell strains
   786-O: human kidney cancer cell strains
   HL-60: human leukemia cell strains
   K562: human leukemia cell strain
   PC-3: human prostate cancer cell strains
   RPMI 1640 culture solution
   MTT: tetrazolium blue
   DMSO: dimethylsulfoxide
   96-well cell culture plates
2. Assays on Inhibitory Activity for Cell Growth
   (1) Cell Culture and Pharmaceutical Treatment
   Cells were inoculated in RPMI 1640 cell culture solution with 10% fetal bovine serum (supplemented with 100 ku/L of penicillin, streptomycin, respectively). The petri dishes were left in a cell incubator containing 5% $CO_2$ under the temperature of 37° C. The medium was changed every 2-3 days, and was digested with 0.25% trypsin solution. The cells were subcultured and collected.
   The cells in the exponential phase were formulated into cell suspensions with desired concentrations using RPMI 1640 cell culture solutions containing 10% fetal bovine serum. The suspensions were added into 96-well cell culture plates according to 3,000-5,000 cells per well (100 μl). After being cultured for 24 hr, 100 μl of assay compounds having different concentrations were added into each well. Four parallel tests were conducted for each well. The supernatants were discarded after being cultured for 72-120 hr. 100 μl of 0.5 mg/ml MTT fresh serum-free culture solutions were added into each well. The resultant supernatants were discarded after being cultured for 4 hr at 37° C. Formazan was dissolved with 200 μl DMSO. The resulting mixture was gently shaken for 15 min. Optical absorption values (OD-values) at 570 nm of detection wavelength and 450 nm of reference wavelength were measured with ELISA reader.
   (2) Data Processing
   The data were represented by x±s. Inhibition Ratio=(OD values in control groups−OD values in administration groups)/OD values in control groups×100%. Anti-cancer effects were represented by maximum inhibition ratio $I_{max}$ and inhibitory concentration 50 ($IC_{50}$). Drawings were obtained with software MicroCal Origin. Inhibition curves of assay compounds for inhibiting the growth of tumor cells were fitted by the four-parameter program Logistic in the software so as to give the inhibitory concentration 50 ($IC_{50}$: μg/ml) for inhibiting the proliferation of tumor cells.
   (3) Results
   The exposure concentrations of the assay compounds were 0.001 μg/ml, 0.003 μg/ml, 0.009 μg/ml, 0.027 μg/ml, 0.082 μg/ml, 0.247 μg/ml, 0.741 μg/ml, 2.222 μg/ml, 6.667 μg/ml and 20 μg/ml. The exposure concentrations of adriamycin (as positive drugs) were 1.25 μg/ml, 5 μg/ml and 20 μg/ml. In 96-well plates, 3,000-5,000 cells were inoculated in each well. Four parallel assays were conducted for each concentration. The inhibition ratios of the compounds for HL-60 cells under the concentration of 1 μM are shown in Table 1. The inhibitory activities of the compounds for various tumor cells are shown in Table 2.

TABLE 1

Inhibition Ratios of Assay Compounds for HL-60 Cells under Concentration of 1 μM

| Compounds | Inhibition Ratio (%) |
| --- | --- |
| Example 1 | 80 |
| Example 4 | 62 |
| Example 5 | 35 |
| Example 6 | 43 |
| Example 7 | 10 |
| Example 8 | 71 |

TABLE 2

Inhibitory Activity of Assay Compounds on Tumor Cells

| Compounds | Inhibitory Concentration 50 for Cell Growth ($IC_{50}$)(nM) | | | |
| --- | --- | --- | --- | --- |
| | PC-3 Cells | A431 Cells | THP-1 | U937 Cells |
| Epirubicin | 110 | 18 | 67 | 10 |
| Example 1 | 10 | 6.3 | 9 | 12 |
| | NCI H460 | NCI H446 | HL-60 | K562 |
| Epirubicin | 25 | | | |
| Example 1 | 14 | 160 | 357 | 44 |
| | Hep G2 | A549 | 786-O | DU-145 |
| Example 1 | 27 | 206 | 74 | 8.6 |

In accordance with the above data, the compounds disclosed in the present invention have inhibitory activity on human cancer cells. The activity of the compound in Example 1 is equal to or better than that of epirubicin and has strong inhibitory effects on the growth of various human tumor cell strains, such as human leukemia K562, human prostate cancer PC-3, lymphoma U937, kidney cancer 786-0, lung cancer A549 and the like. Therefore, the compounds of the present invention have broad spectrum anti-tumor activity

Example 11

Assays on Maximum Tolerated Dose (MTD) In Vivo of Mice

1. Assay Materials (1) Assay animals: 9 Kunming Mice, of which five were male and four were female, with a weight of 20-22 g (purchased from Lab Animals Center of Chinese Academy of Medical Sciences, License No. scxk (jin) 2005-0001)

(2) Assay medicine: compound in Example 1

(3) Materials: 1 ml disposable syringes (Jiangxi Hongda Medical Equipment Group, Lot No. 060928)

2. Assay Method

Kunming mice were 9, of which 5 were male and 4 were female. Each mouse was administered the compound in Example 1 (20 mg/kg, iv) with a dose volume of 20 ml/kg. Intoxication and death of the mice were observed for 14 days.

The process for preparing a solution of the compound in Example 1: 4.53 mg of the compound in Example 1 was weighed and dissolved by adding 40 μL of DMSO (dimethylsulfoxide). 340 μL of RH40 (polyoxyethylene castor oil) were added. After mixing homogeneously, 4.156 mL of physiological saline was added to the mixture. After mixing homogeneously, the mixture was filtered with 0.45 μm filter membrane to give a 1 mg/ml solution of the compound in Example 1.

Observation time: 14 days

Observation indicators: weight, appearance, breath, action, reflection, defecation 3. Assay Results:

Average Weight (g) of Mice after Single Intravenous Injection of Compound in Example 1

| Group | Day 1 | Day 2 | Day 3 | Day 5 | Day 6 | Day 7 | Day 8 | Day 9 | Day 10 | Day 11 | Day 12 | Day 13 | Day 14 |
|---|---|---|---|---|---|---|---|---|---|---|---|---|---|
| 20 mg/kg | 20.9 | 20.2 | 20.4 | 19.7 | 20.2 | 19.8 | 20.0 | 20.1 | 20.5 | 20.4 | 20.4 | 20.8 | 21.1 |

Mortality Rate of Mice after Single Intravenous Injection of Compound in Example 1

| Group | Number of Animals | Death Number | Mortality Rate (%) |
|---|---|---|---|
| Group 20 mg/kg | 9 | 0 | 0 |

The mice were administered with the compound in Example 1 via tail vein. The dose was 20 mg/kg and the dose volume was 20 ml/kg. There were nine mice in total. The mice were observed for 14 days, in which there was no significant change on the weights of the mice and no animal died, while other indicators were not obviously abnormal. The mice were dissected at the end of the test and no abnormal phenomena were observed. The above results demonstrated that the compounds of the present invention have good tolerance on mice.

From the foregoing it will be appreciated that, although specific embodiments of the present application have been described herein for purpose of illustration, various modifications may be made without deviating from the spirit and scope of the present application. Accordingly, the present application is not limited except as by the appended claims.

What is claimed is:

1. A compound of formula (I), a pharmaceutically acceptable salt thereof, a solvate thereof, or a solvate of the pharmaceutically acceptable salt thereof,

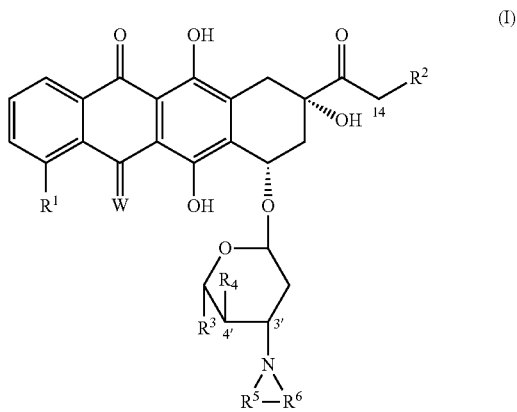

wherein:

$R^1$ represents H, F, OH, optionally substituted hydrocarbyl or optionally substituted hydrocarboxy;

$R^2$ represents H or OH;

W represents O or NH;

$R^3$ represents H, F, OH, optionally substituted hydrocarbyl or optionally substituted hydrocarboxy;

$R^4$ represents F or $OR^7$, wherein $R^7$ represents H or 2-pyranyl;

wherein

is selected from the group consisting of a group represented by formula (II), a group represented by formula (V) and a group represented by formula (VI),

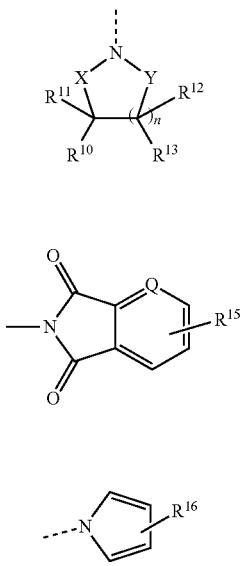

wherein, n represents 1 or 2; X represents C=O or $CR^{21}R^{22}$; Y represents C=O or $CR^{21}R^{22}$; Q represents CH or N; $R^{10}$, $R^{11}$, $R^{12}$, $R^{13}$, $R^{15}$, $R^{16}$, $R^{21}$ and $R^{22}$ separately represent H, F, Cl, CN, OH, $COOC_{1-4}$ hydrocarbyl, $OC_{1-4}$ hydrocarbyl, $C_{1-4}$ hydrocarbyl or $NR^{18}R^{19}$; $R^{18}$ and $R^{19}$ separately represent H or $C_{1-6}$ hydrocarbyl, or $NR^{18}R^{19}$ together represents pyrrolidin-1-yl, piperidin-1-yl or morpholin-1-yl.

2. The compound claim 1, wherein $R^1$ represents H, $CH_3$ or $OCH_3$.

3. The compound of claim 1, wherein $R^3$ represents H, F, $CH_3$, $CH_2CH_3$, OH, $OCH_3$ or $OCH_2CH_3$.

4. The compound of claim 1, wherein the optionally substituted saturated heterocyclic hydrocarbyl, the optionally substituted unsaturated heterocyclic hydrocarbyl, the optionally substituted aromatic heterocyclyl or the optionally substituted fused cyclic group further comprises one or two identical or different other heteroatoms.

5. The compound of claim 1, wherein

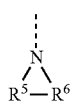

represents a group represented by formula (VI),

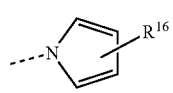

wherein, $R^{16}$ represents H, F, Cl, CN, OH, $CH_3$, $CH_2CH_3$, $CH_2CH_2CH_3$, $OCH_3$, $OCH_2CH_3$, $OCH_2CH_2CH_3$, $COOCH_3$, $COOCH_2CH_3$, $COOCH_2CH_2CH_3$, $N(CH_3)_2$, $N(CH_2CH_3)_2$, pyrrolidin-1-yl, piperidin-1-yl or morpholin-1-yl.

6. The compound of claim 1, wherein

is selected from the group consisting of 1-pyrroly, succinimidyl, glutarimido, butyrolactam-1-yl, valerolactam-1-yl, 3-methyl-pyrro-1-ly, 3-methoxyl-pyrro-1-ly, 3-methyl-succinimidyl, 3-methoxyl-succinimidyl, 3-methyl-glutarimido, 3-methoxyl-glutarimido, 3-methyl-butyrolactam-1-yl, 3-methoxyl-butyrolactam-1-yl, 3-methyl-valerolactam-1-yl, 3-methoxy-valerolactam-1-yl, 4-methyl-valerolactam-1-yl, 4-methoxyl-valerolactam-1-yl, 2-cyanomorpholinyl, 2-pyrrolin-1-yl, and phthalimido.

7. The compound of claim 1, selected from the group consisting of:
  3'-pyrrolyl epirubicin,
  3'-succinimidyl epirubicin,
  3'-glutarimido epirubicin,
  3'-maleimidyl epirubicin,
  3'-(pyridino-(2,3)succinimidyl)epirubicin,
  3'-(benzo-(2,3)succinimidyl)epirubicin, and
  3'-butyrolactamyl epirubicin.

8. A pharmaceutical composition comprising a pharmaceutically acceptable carrier and a therapeutically effective amount of the compound of claim 1.

9. A pharmaceutical composition of claim 8, which is formulated into a dosage form suitable for oral administration, buccal administration, intravenous injection, intraperitoneal injection, subcutaneous injection, intramuscular injection, nasal drops, eye drops, inhalation, rectal administration, vaginal administration or epidermal administration.

10. A pharmaceutical composition of claim 9, wherein the dosage form is a powder injection, a lyophilized powder injection, a water injection, an emulsion or a suspension.

11. A process for preparing a compound of formula (I), a pharmaceutically acceptable salt thereof, a solvate thereof, or a solvate of the pharmaceutically acceptable salt thereof,

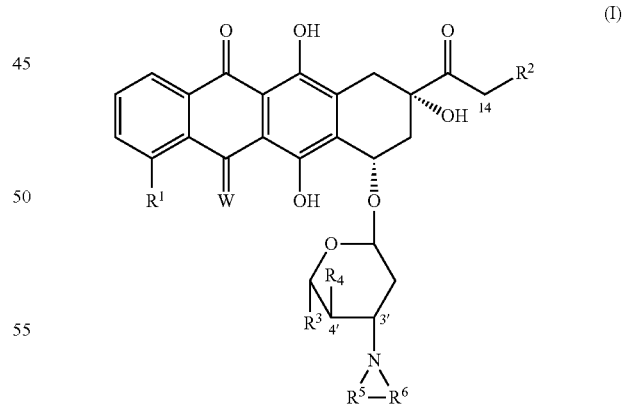

wherein:
$R^1$ represents H, F, OH, optionally substituted hydrocarbyl or optionally substituted hydrocarboxy;
$R^2$ represents H or OH;
W represents O or NH;
$R^3$ represents H, F, OH, optionally substituted hydrocarbyl or optionally substituted hydrocarboxy;
$R^4$ represents F or $OR^7$, wherein $R^7$ represents H or 2-pyranyl;

wherein

is selected from the group consisting of a group represented by formula (II), a group represented by formula (V) and a group represented by formula (VI),

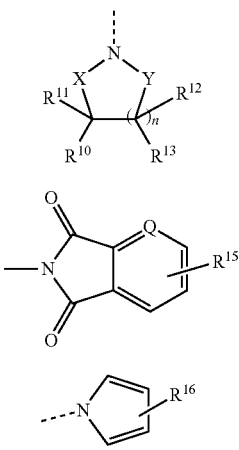

wherein, n represents 1 or 2; X represents C=O or $CR^{21}R^{22}$; Y represents C=O or $CR^{21}R^{22}$; Q represents CH or N; $R^{10}$, $R^{11}$, $R^{12}$, $R^{13}$, $R^{15}$, $R^{16}$, $R^{21}$ and $R^{22}$ separately represent H, F, Cl, CN, OH, $COOC_{1-4}$ hydrocarbyl, $OC_{1-4}$ hydrocarbyl, $C_{1-4}$ hydrocarbyl or $NR^{18}R^{19}$; $R^{18}$ and $R^{19}$ separately represent H or $C_{1-6}$ hydrocarbyl, or $NR^{18}R^{19}$ together represents pyrrolidin-1-yl, piperidin-1-yl or morpholin-1-yl the process comprising:

reacting a compound represented by formula (VII) or a salt formed from a mixture of a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula (VIII) to obtain the compound represented by formula (I) in presence of an acidic agent or/and a basic agent,

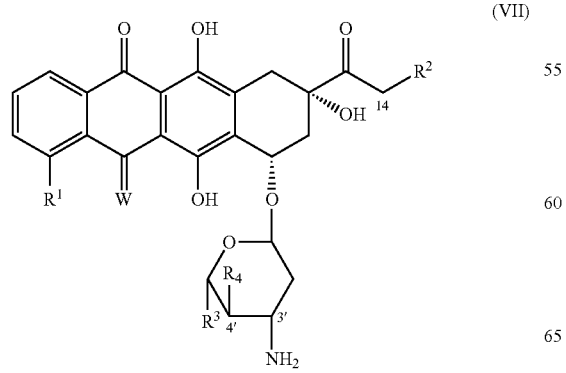

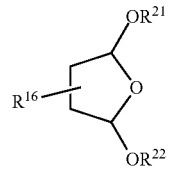

wherein $R^1$, $R^2$, $R^3$, $R^4$ and W groups in formula (VII) are identical to $R^1$, $R^2$, $R^3$, $R^4$ and W groups in formula (I), $R^{16}$ group in formula (VIII) is identical to $R^{16}$ group in formula (VI), and $R^{21}$ and $R^{22}$ separately represent H or optionally substituted hydrocarbyl; or reacting a compound represented by formula (VII) or a salt formed from a mixture of a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula (IX) to obtain a compound represented by formula (X), and giving the compound represented by formula (I) by subjecting the compound represented by formula (X) to a dehydrating agent,

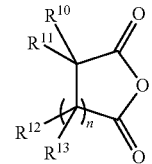

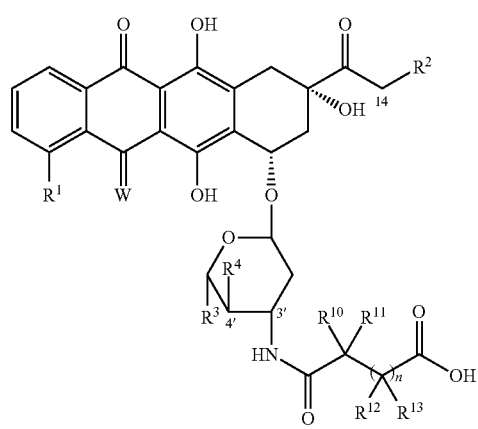

wherein $R^{10}$, $R^{11}$, $R^{12}$, $R^{13}$ groups and n in formula (IX) are identical to $R^{10}$, $R^{11}$, $R^{12}$, $R^{13}$, groups and n in formula (II); $R^{10}$, $R^{11}$, $R^{12}$, $R^{13}$ groups and n in formula (X) are identical to $R^{10}$, $R^{11}$, $R^{12}$, $R^{13}$ groups and n in formula (II), and $R^1$, $R^2$, $R^3$, $R^4$ and W groups in formula (X) are identical to $R^1$, $R^2$, $R^3$, $R^4$ and W groups in formula (VII); or reacting a compound represented by formula (VII) or a salt formed from a mixture of a compound represented by formula (VII) and one or more acids selected from the group consisting of hydrochloric acid, sulfuric acid, phosphoric acid, formic acid, acetic acid, methanesulfonic acid, benzenesulfonic acid and p-toluenesulfonic acid, with a compound represented by formula ⑧ to obtain a compound represented by formula ⑨ or ⑩, and giving the compound represented by formula (I) by subjecting the compound represented by formula ⑨ or ⑩ to a dehydrating agent,

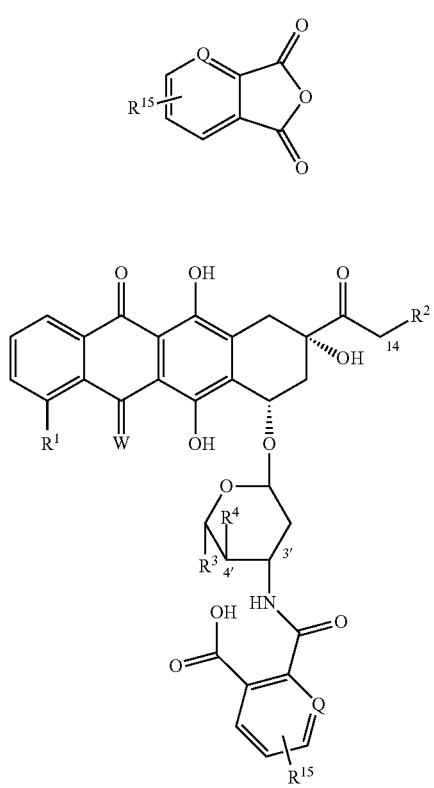

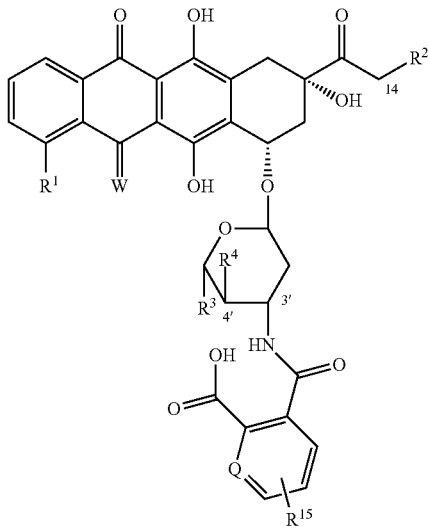

wherein $R^{15}$ and Q groups in formula ⑧ are identical to $R^{15}$ and Q groups in formula (V), $R^{15}$ and Q groups in formula ⑨ are identical to $R^{15}$ and Q groups in formula (V), $R^1$, $R^3$, $R^4$, $R^2$ and W groups in formula ⑨ are identical to $R^1$, $R^3$, $R^4$, $R^2$ and W groups in formula (VII), $R^{15}$ and Q groups in formula ⑩ are identical to $R^{15}$ and Q groups in formula (V), and $R^1$, $R^3$, $R^4$, $R^2$ and W groups in formula ⑦ are identical to $R^1$, $R^3$, $R^4$, $R^2$ and W groups in formula (VII).

12. A method for inhibiting or relieving diseases or conditions caused by abnormal cell proliferation, comprising administering to a subject in need thereof a therapeutically effective amount of a compound of claim 1.

13. A method of claim 12, wherein the diseases or conditions caused by abnormal cell proliferation are cancer.

14. A method of claim 13, wherein the cancer is selected from the group consisting of prostate cancer, breast cancer, ovarian cancer, liver cancer, stomach cancer, small cell lung cancer, non-small cell lung cancer, intestinal cancer, colon cancer, Hodgkin's disease, non-Hodgkin's lymphoma, rectal cancer, brain cancer, urethral carcinoma, kidney cancer, bladder cancer, uterine cancer, pancreatic cancer, head and neck cancer, melanoma, various leukemia, lymphoma and multiple myeloma.

\* \* \* \* \*